US00PP15175P3

(12) United States Plant Patent
Dirr

(10) Patent No.: US PP15,175 P2
(45) Date of Patent: Sep. 28, 2004

(54) ***HYDRANGEA MACROPHYLLA* PLANT NAMED 'LADY IN RED'**

(50) Latin Name: *Hydrangea macrophylla*
Varietal Denomination: Lady in Red

(75) Inventor: Michael A. Dirr, Watkinsville, GA (US)

(73) Assignee: University of Ga. Research Foundation, Inc., Athens, GA (US)

( * ) Notice: Subject to any disclaimer, the term of this patent is extended or adjusted under 35 U.S.C. 154(b) by 0 days.

(21) Appl. No.: 10/262,453

(22) Filed: Oct. 1, 2002

(65) Prior Publication Data

US 2004/0064864 P1 Apr. 1, 2004

(51) Int. Cl.[7] ..... A01H 5/00
(52) U.S. Cl. ..... Plt./250
(58) Field of Search ..... Plt./250

(56) References Cited

U.S. PATENT DOCUMENTS

| | | | | | |
|---|---|---|---|---|---|
| PP9,462 | P | * | 3/1996 | Hofstede et al. | Plt./250 |
| PP10,152 | P | * | 12/1997 | Sousa | Plt./250 |
| PP10,371 | P | * | 5/1998 | Ebihara | Plt./250 |
| PP10,372 | P | * | 5/1998 | Ebihara | Plt./250 |
| PP10,440 | P | * | 6/1998 | Ebihara | Plt./250 |
| PP10,906 | P | * | 5/1999 | Rampp et al. | Plt./250 |
| PP10,912 | P | * | 5/1999 | Rampp et al. | Plt./250 |
| PP10,928 | P | * | 6/1999 | Rampp et al. | Plt./250 |
| PP10,930 | P | * | 6/1999 | Rampp et al. | Plt./250 |
| PP11,405 | P | * | 6/2000 | Usrey | Plt./250 |

* cited by examiner

*Primary Examiner*—Bruce R. Campell
*Assistant Examiner*—W. C. Haas
(74) *Attorney, Agent, or Firm*—Glasgow Law Firm, PLLC

(57) ABSTRACT

*Hydrangea macrophylla* 'Lady in Red' is a lacecap with the sterile florets of the inflorescences maturing from pale pink to burgundy rose. It has lustrous reddish-purple leaf venation, petiole and stem color, and the foliage develops a red-purple fall color. The plant has high mildew resistance.

6 Drawing Sheets

Botanical designation: *Hydrangea macrophylla* (Thunb.) Ser. 'Lady in Red'.

BACKGROUND OF THE INVENTION

1. Field of the Invention

The present invention relates to a new and distinct variety of *Hydrangea macrophylla* (Thunb.) Ser., a member of the Hydrangeaceae family. *Hydrangea macrophylla* 'Lady in Red' is the result of a controlled breeding program at the University of Georgia, Athens, Ga. and the Center for Applied Nursery Research, Dearing, Ga. The variety originated from open-pollinated *Hydrangea macrophylla* 'Otaksa' (unpatented) and one single plant was selected from 265 seedlings. The plant is used primarily as an ornamental. The variety, 'Lady in Red', has been asexually reproduced by cuttings for 2 years. The novel leaf, stem, flower, and mildew resistance were consistent through these generations.

2. Description of Relevant Prior Art

'Lady in Red' is distinguished from its parent (a mophead) and all other varieties of *Hydrangea macrophylla* known to the inventor by its lustrous reddish-purple stem, leaf venation, petiole color, reddish-purple fall color and high mildew resistance. Only *Hydrangea macrophylla* 'Nigra' (black-purple stems) (unpatented) and 'Preziosa' (reddish-purple stems) (unpatented) are noted for rich stem color. However, both have mophead flowers, are highly mildew susceptible, and do not develop the rich reddish-purple fall color.

SUMMARY OF THE INVENTION

*Hydrangea macrophylla* 'Lady in Red' develops lustrous reddish-purple stems, leaf venation and petiole coloration.

The leaves turn reddish-purple in fall and are highly resistant to mildew. The lacecap sterile florets (sepals) open pinkish-white maturing to burgundy-rose.

BRIEF DESCRIPTION OF DRAWINGS

The accompanying illustrations show characteristics of the new cultivar in photographs as true to color as is reasonably possible to make in illustrations of this nature.

BOTANICAL DESCRIPTION OF THE PLANT

Figure 1:
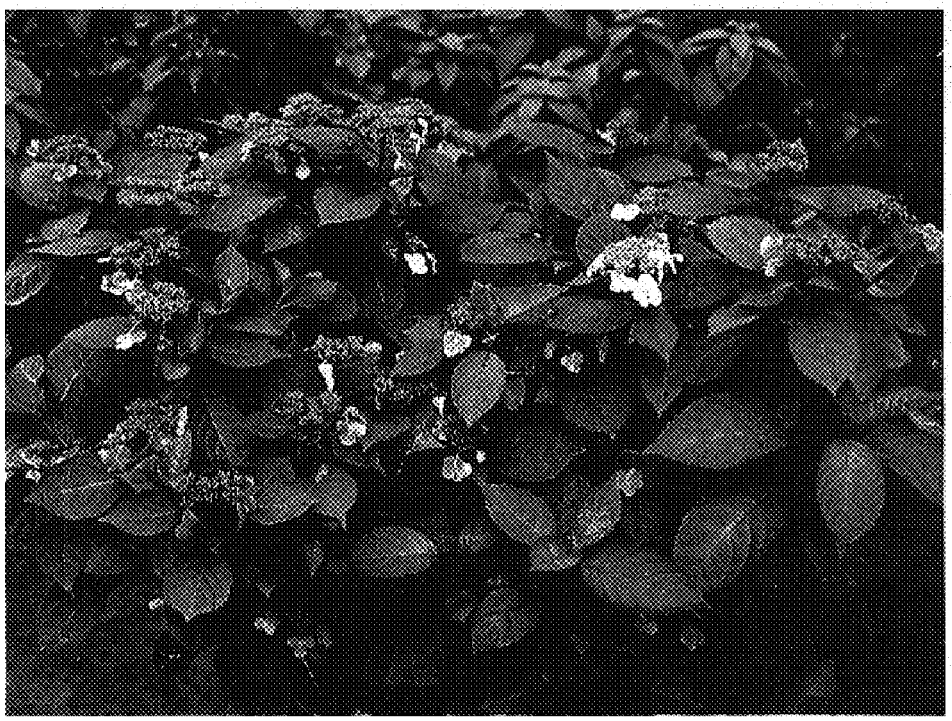
FIG. 1 shows a 3-year-old unpruned plant in a 27 liter container.
Figure 2:
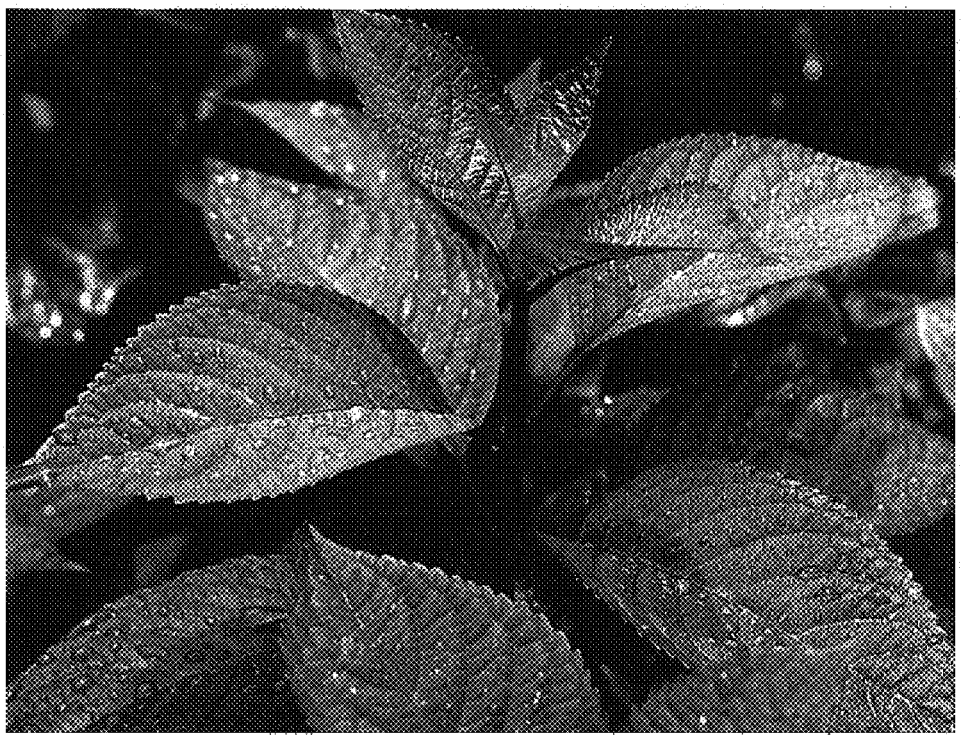
FIG. 2 illustrates the summer leaf color and texture.
Figure 3:
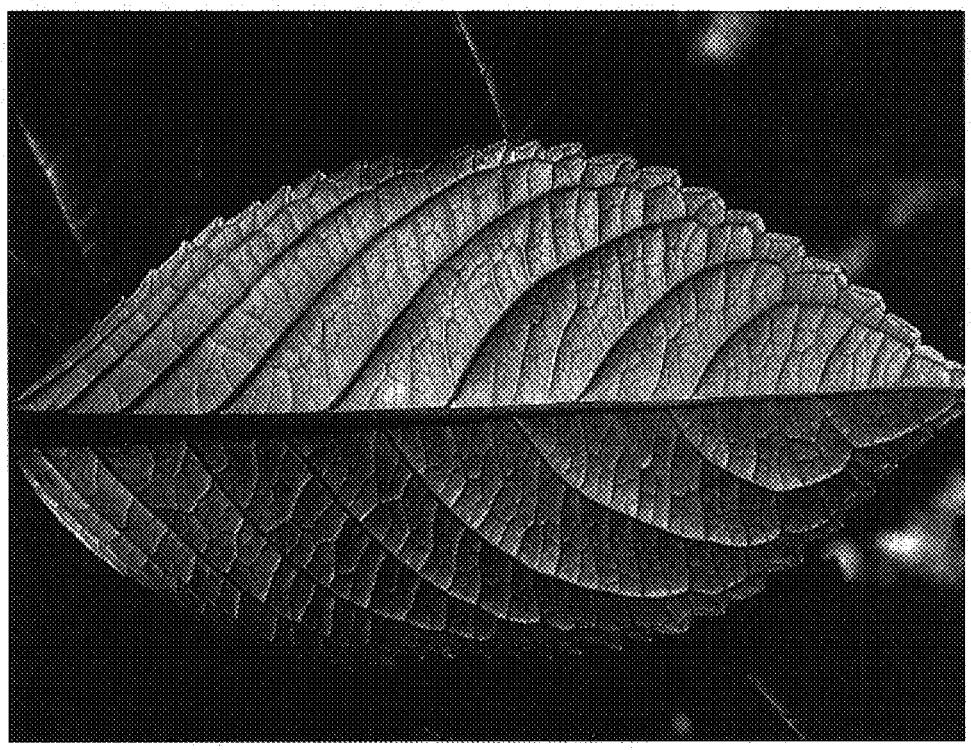
FIG. 3 illustrates the lower surface of the leaf with the prominent, reddish-purple raised veins.
Figure 4:
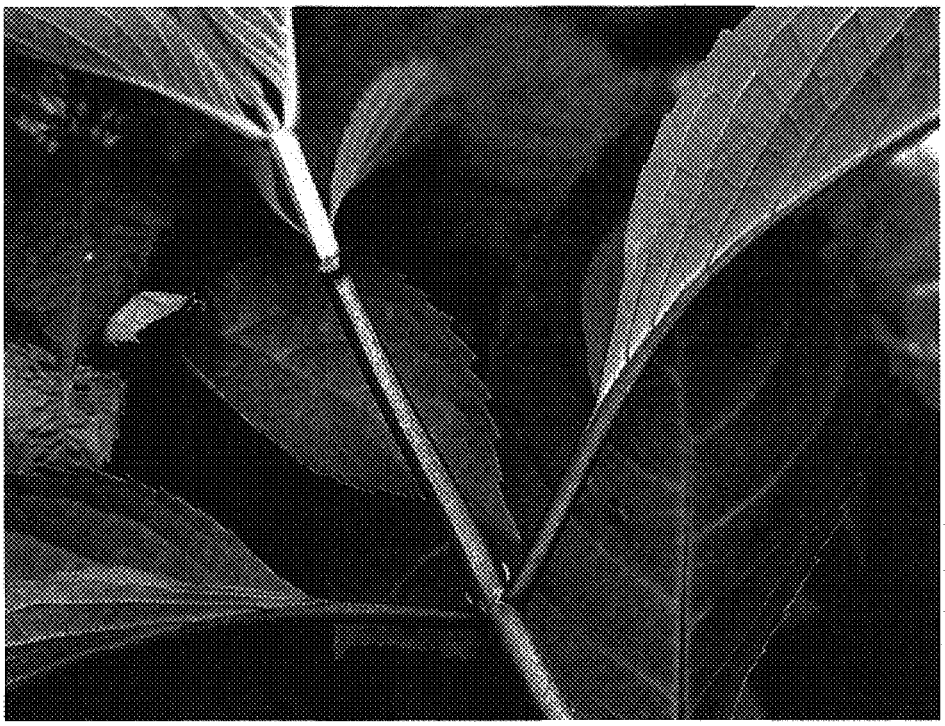
FIG. 4 illustrates the reddish-purple stem and petiole.
Figure 5:
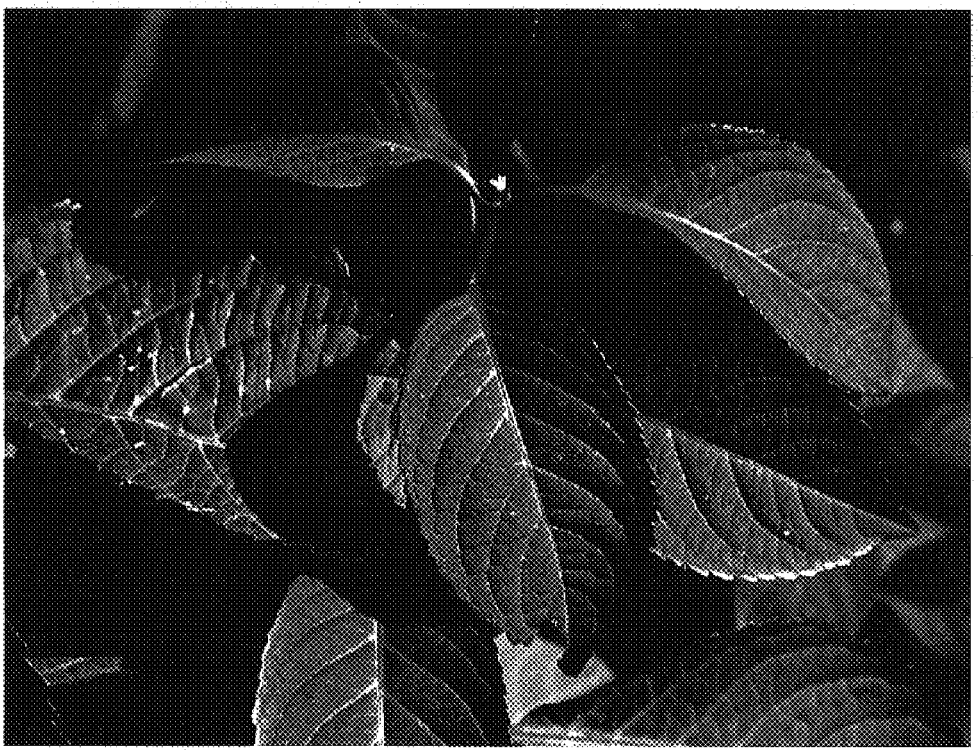
FIG. 5 illustrates the reddish-purple fall color.
Figure 6:
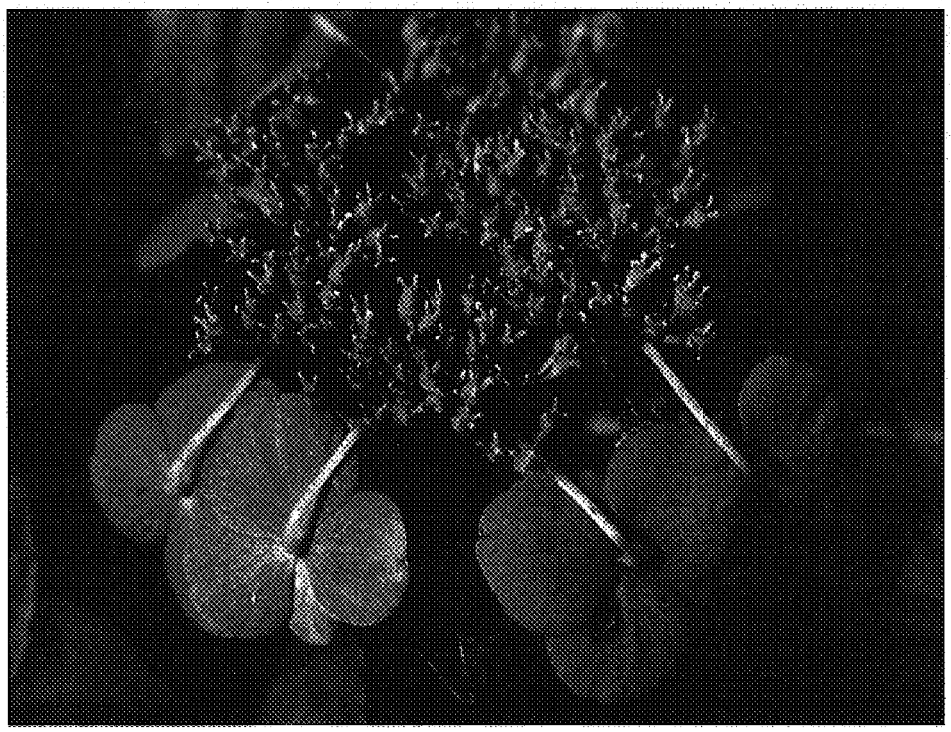
FIG. 6 illustrates the burgundy-rose mature sepals.

A detailed description of *Hydrangea macrophylla* 'Lady in Red' follows. Colors are based on The Royal Horticultural Colour Chart (1995). All measurements/characteristics were taken from a 3-year-old plant in a 26.6 liter nursery container grown outdoors under 50% shade at Dearing, Ga. (USDA Zone 7.b). Plants flag or droop when grown in direct sun and 30% to 50% shade is recommended. Measurements of leaves/stems and floral characteristics are based on 10 to 20 samples.

Classification:

*Botanical.*—*Hydrangea macrophylla* (Thunb.) Ser. 'Lady in Red'.

*Parentage.*—Open-pollinated seedling of *Hydrangea macrophylla* 'Otaksa'.

*Propagation.*—Vegetatively by cuttings.

Plant:

*Size.*—58 cm high, 91.4 cm wide in 3-years.

*Habit.*—Mounded deciduous shrub, multistemmed and extremely compact.

*Branching.*—Many breaks (shoots) from base of one-year plants, i.e., freely branching. A twice pruned, 1 year plant grown in a 3 gallon pot had 25 to 30 branches, ranging in length from 20–50 cms.

Leaf:

*Shape.*—Ovate.

*Base.*—Cuneate.

*Apex.*—Acute to abruptly acuminate.

*Size.*—Length 12.4 cm, width 6.7 cm.

*Arrangement.*—Opposite.

*Margin.*—Coarsely serrate.

*Texture/substance.*—Thickish; glabrous on upper and lower surfaces; eight prominent raised veins on lower surface.

*Petioles.*—2.4 cm long, glabrous, grooved above, rounded below. Color: Greyed-Purple Group 183A.

*Mature leaf color.*—Summer color varies with nutrition and intensity of sunlight. Upper leaf surface typically Yellow-Green Group 147A; lower surface Green Group 138B. Fall color is Red-Purple Group 59A. Petiole and lower leaf surface veins are Greyed-Purple Group 183A.

Stems:

*Thickness.*—0.5 cm to 0.6 cm diameter.

*Texture.*—Stout, terete, glabrous, lustrous.

*Internodes.*—5.2 cm.

*Color.*—Greyed-Purple Group 183A.

*Hardiness.*—USDA (1990) Zone 7 (17.8 C. to 12.2 C.) to 9 (6.7 C. to 1.1 C.).

*Vigor.*—Vigorous; rooted cuttings transplanted in spring develop a full 11.4 liter container by fall (Athens, Ga.).

Inflorescence:

*Bloom period.*—May to August, Athens and Dearing, Ga.

*Flower arrangement.*—Corymb, lacecap, 150 to 200 fertile flowers in center, 5 to 10 sterile florets around periphery.

*Shape of inflorescence.*—Flat-topped.

*Inflorescence size.*—10–15 cm in diameter and 2.5 to 5 cm in depth.

*Fertile flowers.*—Glabrous, 5 ovate, entire sepals, acute at apex and base, each 0.4 cm long, 0.2 cm wide, entire flower 0.8 cm diameter, pedicel 0.6 cm long, flower buds globose, 0.4 cm high, 0.4 cm wide, color of buds and open petals Violet Group 84B.

*Sterile florets.*—3 to 4 sepals per cluster (showy floret), each rounded, entire, 1.6 cm long, 1.6 cm wide, collection of 3 to 4 sepals, 2.5 cm to 3.2 cm diameter.

*Color.*—Sterile florets: Upper surface — Purple Group 75C; lower surface — White Group 155D. Sepals, after fertile flowers are pollinated, turn Yellow-Green Group 144A on upper surface, Red Group 46A on lower surface.

*Fragrance.*—None noted.

*Persistence of flowers.*—Fertile flowers open over a 2 to 3 week period; sterile florets are effective for 2 to 3 months.

Reproductive system:

*Fertile flowers.*—Five stamens on fertile flowers; anther comprised of 2 sacs measuring 0.3 cm long by 0.015 cm wide and filament 0.64 to 0.95 cm long and extremely fine, essentially immeasurable; color Violet-Blue Group 94B, pollen: color white Group 155D; stigma: 3 per ovary.

*Fruit.*—Fertile capsule, urn shaped, 0.5 cm long, 0.3 cm wide, color Brown Group 200B.

Root structure: The root structure varies according to the repotting protocol adopted, the potting medium used, and the irrigation and fertilization procedures, and does not significantly influence or impact the ornamental characteristics which define this plant.

I claim:

1. A new and distinct variety of *Hydrangea macrophylla* plant, substantially as herein described and illustrated.

* * * * *